(12) United States Patent
Gainer et al.

(10) Patent No.: US 8,426,392 B2
(45) Date of Patent: Apr. 23, 2013

(54) METHOD FOR PROVIDING EMERGENCY CONTRACEPTION

(75) Inventors: Erin Gainer, Paris (FR); Henri Camille Mathe, Paris (FR)

(73) Assignee: Laboratoire HRA-Pharma, Paris (FR)

( * ) Notice: Subject to any disclaimer, the term of this patent is extended or adjusted under 35 U.S.C. 154(b) by 185 days.

(21) Appl. No.: 12/633,885

(22) Filed: Dec. 9, 2009

(65) Prior Publication Data

US 2011/0136770 A1 Jun. 9, 2011

(51) Int. Cl.
*A61K 31/56* (2006.01)

(52) U.S. Cl.
USPC .......................................... 514/170; 514/182

(58) Field of Classification Search .................. 514/170, 514/182
See application file for complete search history.

(56) References Cited

PUBLICATIONS

Creinin et al., Obstetrics & Gynecology, 2006;108(5):1089-1097.*
Creinin, Mitchell etc. "Progesterone Receptor Modulator for Emergency Contraception", Obstetrics & Gynecology, 2006, 108 (5): 1089-1097.
New Product Review (Oct. 2009) Ulipristal Acetate by Faculty of Sexual and Reproductive Healthcare Clinical Effectiveness Unit.
Summary of Product Characteristics for ulipristal acetate by European Medicines Agency (EMEA) May 15, 2009.
European Public Assessment Report (EPAR) for ulipristal acetate by European Medicines Agency (EMEA)—summary for the public (May 2009).
CHMP Assessment Report for ulipristal acetate by European Medicines Agency (EMEA) (May 2009).

* cited by examiner

*Primary Examiner* — San-Ming Hui
(74) *Attorney, Agent, or Firm* — Michael A. Davitz

(57) ABSTRACT

The invention provides a method for providing emergency contraception in a female subject, comprising providing the subject with a therapeutically effective amount of ulipristal acetate in an oral dosage form before, during or after a meal. The invention further provides a kit comprising i) an oral dosage form comprising ulipristal acetate and ii) a printed matter stating that ulipristal acetate may be taken with or without food.

9 Claims, 2 Drawing Sheets

METHOD FOR PROVIDING EMERGENCY CONTRACEPTION

Figure 1:
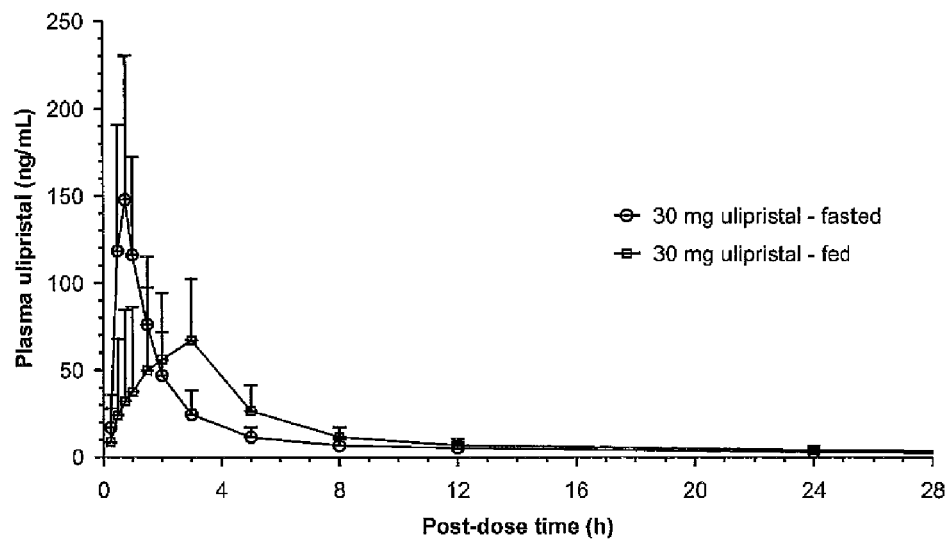

The present invention relates to a method for providing emergency contraception, comprising orally administering ulipristal acetate.

BACKGROUND TO THE INVENTION

Emergency contraception (EC), indicated for the prevention of pregnancy following unprotected intercourse or a known or suspected contraceptive failure, is a woman's second chance for primary prevention of pregnancy. For decades, various high-dose estrogen-progestin regimens have been prescribed by experienced gynecologists for EC, generally involving the off-label administration of high doses of combined oral contraceptive pills. It is only in the mid-nineteen-nineties that dedicated products appeared, following requests from regulatory agencies and women's groups for properly labelled and packaged preparations. Initially, dedicated products consisted of high-dose estrogen-progestin preparations. In 1999, based on WHO publications of randomized clinical trials demonstrating that 0.75 mg levonorgestrel twice was as effective as combined estrogen-progestin preparations, HRA Pharma's NorLevo® became the first progestin-only EC to be granted a marketing authorization in Western countries. Since that time, several preparations have been approved elsewhere in the world (e.g. Plan B®, Levonelle®, Postinor®), and currently the standard of care for EC within 72 hours of unprotected intercourse is the administration of 1.5 mg of levonorgestrel, either in a single dose or in two 0.75 mg doses taken 12-24 hours apart. A number of countries have granted non-prescription status to these preparations based on levonorgestrel's well-characterized safety profile and limited contraindications.

Although EC with 1.5 mg of levonorgestrel has undoubtedly contributed to the prevention of unwanted pregnancies, it has its limitations in terms of efficacy: its efficacy rate drops significantly with the time elapsed since unprotected intercourse. Reported pregnancy rates from WHO trials rise from approximately 1.5 to 2.6%, respectively, for intake 0 to 24 hrs as compared to intake 48-72 hrs after intercourse. In addition, for a woman who presents for EC more than 72 h after intercourse, the only available method with a proven efficacy is the insertion of a copper intra-uterine device (although not approved or labelled for such use in the United States), although use is limited by both availability and the need for insertion by a skilled health-care professional.

Ulipristal acetate (also referred to as CDB-2914, VA2914, HRP-2000 and RTI 3021-012) is an orally-active selective progesterone receptor modulator (SPRM) that has been developed for emergency contraception. Ulipristal acetate inhibits or delays ovulation in a dose-dependent fashion. In a double-blind non-inferiority trial, ulipristal acetate was shown to be as efficacious as levonorgestrel for preventing pregnancy when used within 72 hours of unprotected intercourse (Creinin et al, Obstetrics & Gynecology 2006; Vol. 108; No. 5: 1089-97).

SUMMARY OF THE INVENTION

Because of the emergency nature of the administration, there is a need to provide both the patient and healthcare provider with information about the effects of food on the plasma levels of ulipristal acetate that can be achieved. The inventors have unexpectedly found that therapeutically effective levels of drug can be achieved with or without food.

The invention thus provides a method for providing emergency contraception in a female subject, comprising providing the subject with a therapeutically effective amount of ulipristal acetate in an oral dosage form before, during or after a meal.

The invention further provides a kit comprising i) an oral dosage form comprising ulipristal acetate and ii) a printed matter stating that ulipristal acetate may be taken with or without food. Preferably, the printed matter states that $C_{max}$ decreases by at least about 45%, AUC increases by at least 20% and $t_{max}$ is delayed by at least about 1.5 hours when ulipristal acetate is administered during or after a meal, compared with administration of ulipristal acetate before a meal or in a fasting state.

Preferably the oral dosage form is a tablet. Advantageously the oral dosage form comprises 30 mg ulipristal acetate.

LEGENDS TO THE FIGURES

FIG. 1 is a graph that shows average (+ Standard deviation) ulipristal acetate plasma concentration vs. Time profile. Linear-linear scale, detail over 24 post dose.

Figure 2:
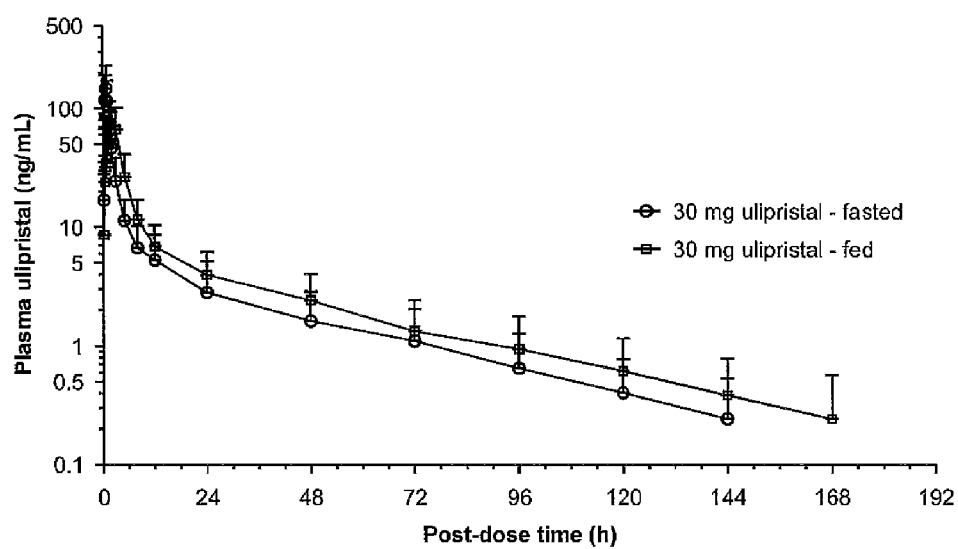

FIG. 2 is a graph that shows average (+ Standard deviation) ulipristal acetate plasma concentration vs. Time profile. Log-linear scale.

Figure 3:
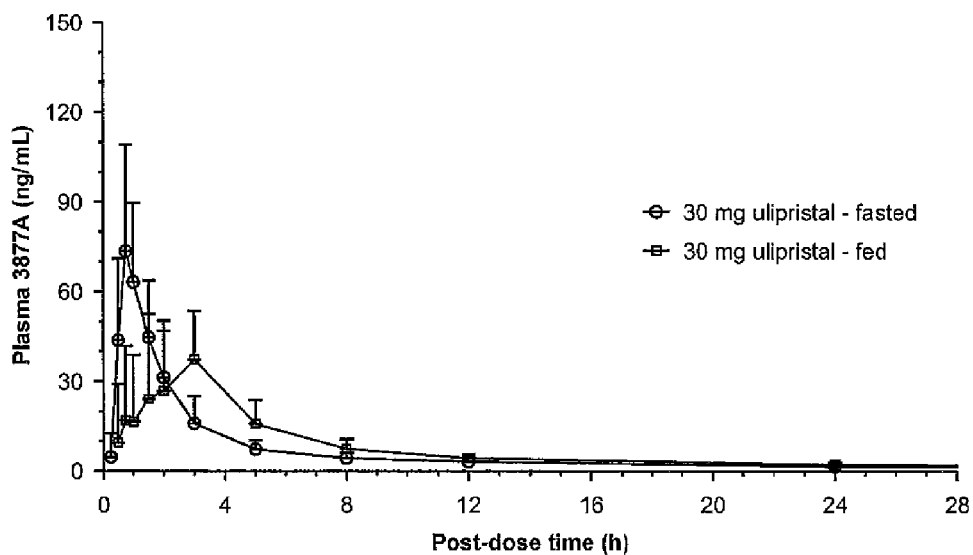

FIG. 3 is a graph that shows average (+ Standard deviation) metabolite 3877A plasma concentration vs. Time profile. Linear-linear scale, detail over 24 post dose.

Figure 4:
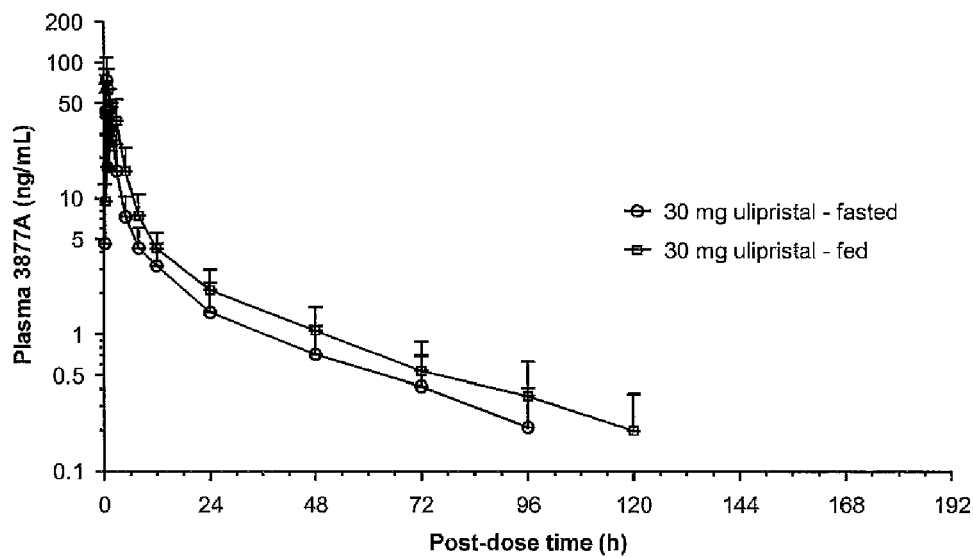

FIG. 4 is a graph that shows average (+ Standard deviation) metabolite 3877A plasma concentration vs. Time profile. Log-linear scale.

DETAILED DESCRIPTION OF THE INVENTION

Ulipristal acetate, formerly known as CDB-2914, designates within the context of this application 17α-acetoxy-11β-[4-N,N-dimethylamino-phenyl)-19-norpregna-4,9-diene-3,20-dione, represented by formula I:

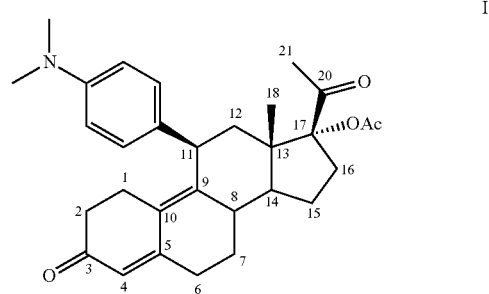 [SMILES: CC(=O)O[C@]1(C(C)=O)CCC2C3CCC4=CC(=O)CCC4=C3[C@@H](c3ccc(N(C)C)cc3)C[C@@]21C]

Ulipristal acetate, and methods for its preparation, are described e.g., in U.S. Pat. Nos. 4,954,490; 5,073,548, and 5,929,262, as well as in international patent applications WO2004/065405 and WO2004/078709, incorporated herein by reference.

Its main metabolite is monodemethylated CDB-2914 (CDB-3877A), that is 17α-acetoxy-11β-[4-N-methylamino-phenyl)-19-norpregna-4,9-diene-3,20-dione.

A specific food interaction study was conducted, in which the pharmacokinetic profile of ulipristal acetate and its main metabolite 3877A was evaluated after single administration of a 30-mg ulipristal acetate micronized tablet either under fasted conditions or after a high-fat breakfast. The main pharmacokinetic parameters were evaluated, including maximum plasma concentration (Cmax), area under the drug concentration curve (AUC) from time 0 to time of last determinable concentration or to infinity, and the time to maximum plasma concentration ($t_{max}$).

Dosing with food significantly reduced the absorption rate of ulipristal acetate (40-45% lower Cmax and by a delay in $t_{max}$ of about 1.5 h for both ulipristal acetate and 3877A) but increased the extent of absorption (20-25% increase in AUC of both ulipristal acetate and of 3877A).

However despite the food effect on the pharmacokinetic parameters, the same therapeutic efficacy in emergency contraception was obtained. On this basis, according to the invention, ulipristal acetate can be taken with or without food.

The subject, who may be also designated by the term "patient", may be any woman in need of an emergency contraception.

Any woman of reproductive age may need emergency contraception at some point to avoid an unintended pregnancy. It is meant to be used in situations of unprotected intercourse, such as:
when no contraceptive has been used;
when there is a contraceptive failure or incorrect use, including:
  condom breakage, slippage, or incorrect use;
  non-compliance with dosage regimen for combined oral contraceptive pills;
  non-compliance with dosage regimen for progestogen-only pill (minipill);
  more than two weeks late for a progestogen-only contraceptive injection (depot-medroxyprogesterone acetate or norethisterone enanthate);
  more than seven days late for a combined estrogen-plus-progestogen monthly injection;
  dislodgment, delay in placing, or early removal of a contraceptive hormonal skin patch or ring;
  dislodgment, breakage, tearing, or early removal of a diaphragm or cervical cap;
  failed coitus interruptus (e.g., ejaculation in vagina or on external genitalia);
  failure of a spermicide tablet or film to melt before intercourse;
  miscalculation of the periodic abstinence method or failure to abstain on fertile day of cycle;
  IUD expulsion; or in cases of sexual assault when the woman was not protected by an effective contraceptive method.

According to the invention, ulipristal acetate may be administered with or without food. The term "with food" refers to administration of ulipristal acetate simultaneously with food ingestion or before or after food ingestion.

In one embodiment, the ulipristal acetate is administered after a meal, preferably at least about 30 minutes, preferably about at least one hour, preferably at least about 2 hours, preferably at least 3 hours, after a meal.

In another embodiment, the ulipristal acetate is administered before a meal, preferably at least about 30 minutes, preferably about at least one hour, preferably at least about 2 hours, preferably at least 3 hours, before a meal.

In preferred embodiment, it is provided a method for providing emergency contraception in a female subject, comprising providing the subject with a therapeutically effective amount of ulipristal acetate in an oral dosage form after a meal, wherein $C_{max}$ decreases by at least 20%, preferably at least 45%, e.g. from about 20 to about 60%, AUC increases by at least 5%, preferably at least 20%, e.g. from about 5 to about 50%, and/or $t_{max}$ is delayed by at least about 1.5 hours when compared with administration of ulipristal acetate before a meal or in a fasting state.

More particularly the meal may have a high fat content.

Preferably the efficacy on emergency contraception is sustained, despite the food effect.

The subject may be administered with said dosage a few days after unprotected intercourse, e.g. within 72 hours after unprotected intercourse.

Ulipristal acetate is preferably in form of a tablet or a capsule, preferably a tablet.

In a preferred embodiment, it is provided as pharmaceutical tablet for oral administration, comprising ulipristal acetate in an amount of 3 to 18 wt %, together with the following excipients: a diluent in an amount of 60 to 95 wt %, a binding agent in an amount of 1 to 10 wt %, croscarmellose sodium in an amount of 1 to 10 wt %, and magnesium stearate in an amount of 0 to 5 wt %.

According to preferred embodiments, the composition, preferably in form of a tablet, comprises 10% wt ulipristal acetate and is designed to contain from 5 to 50 mg ulipristal acetate, preferably 10, 20, or 30 mg.

The diluent may be selected from any pharmaceutically acceptable agent or combination of agents that increases the bulk quantity of ulipristal acetate so that production of a compressed tablet of practical size is possible. In a preferred embodiment, the diluent is selected from the group consisting of a monosaccharide, a disaccharide, a derivative polyol of a monosaccharide and hydrates thereof. The term 'derivative polyol of a monosaccharide' stands for a sugar alcohol such as mannitol, xylitol or sorbitol. Preferably the diluent is selected from the group consisting of lactose monohydrate and mannitol. In a most preferred embodiment, the diluent is lactose monohydrate is an amount of 65 to 92 wt %, more preferably 70-85 wt %.

The binding agent, or binder, may be selected from any pharmaceutically acceptable agent (or combination of agents) which imparts cohesive qualities to powdered materials. The binding agent may be selected from starch, gelatin, sugars such as cellulose derivatives, and natural and synthetic gums may be used. Advantageously, the binding agent of the tablet is selected from the group consisting of polymers. The binding agent may be a natural polymer material such as polysaccharide, or a synthetic polymer such as a plastic polymer. Preferably, the binding agent is hydroxypropyl methyl cellulose and/or povidone. In a preferred embodiment, the binding agent is or comprises povidone, preferably 1.5% to 8.5 wt % of povidone, even more preferably between 3-7 wt %, most preferably about 5 wt % povidone. The tablets preferably comprise croscarmellose sodium. Croscarmellose sodium is a disintegrant, e.g., facilitates break-up of the tablet. Croscarmellose sodium may be used alone or in combination with other disintegrants, preferably alone. It is preferably present in an amount of 1 to 10 wt/%, preferably 1.5 to 8.5 wt %, and more preferably 4.5 to 5.5 wt %, or even more preferably about 5 wt %.

In preferred embodiments, the tablets of the present invention contain magnesium stearate. While magnesium stearate may be used in combination with other lubricants, it is preferably used alone, in an amount comprised between 0.5 and 5 wt %.

Preferably, the tablet according to the present invention comprises lactose monohydrate as a diluent and povidone as a binding agent.

In a more specific embodiment, the tablet comprises: ulipristal acetate 5 to 15 wt %, lactose monohydrate 71 to 87 wt %, povidone 4.5 to 5.5 wt %, croscarmellose sodium 4.5 to 5.5 wt % and magnesium stearate 1 to 4 wt %, where the total percentage adds up to 100.

In an even more specific embodiment, the tablet comprises: ulipristal acetate 10%, lactose monohydrate 79 wt %, povidone 5 wt %, croscarmellose sodium 5 wt % and magnesium stearate 1 wt %.

Tablets may be prepared according to techniques known per se in the art. Suitable methods include direct compression ("dry blending"), dry granulation followed by compression, and wet granulation followed by drying and compression. Several methods include the use of compacting roller technology such as a chilsonator or drop roller, or molding, casting, or extrusion technologies. The tablet can be a coated tablet or an uncoated tablet.

In the preparation of the tablets, commercial mixtures comprising diluents and binding agents may be used, such as Avicel® (microcristalline cellulose), Starlac® (lactose monohydrate 85% with maize starch 15%) or, Ludipress® (lactose monohydrate 93% with Povidone 7%).

The subject is provided with a kit comprising i) an oral dosage form comprising ulipristal acetate and ii) a printed matter that informs female subjects that administration of ulipristal acetate with food results in a decreased Cmax, a delayed $t_{max}$, and/or a higher mean AUC compared with administration in fasted state.

More specifically the printed matter informs the subjects that administration of ulipristal acetate with a high-fat breakfast results in approximately 45% lower mean Cmax, a delayed Tmax (from a median of 0.75 hours to 3 hours) and 25% higher mean AUC0-∞ compared with administration in a fasted state.

Preferably the printed matter further informs the subjects that the oral dosage form of ulipristal acetate can be taken with or without food.

Such printed matter serves as a labelling for the medicament. For instance it is conveniently a leaflet inserted into the packaging of the medicament, or it may be the packaging itself, on which the information is printed.

The figures and examples illustrate the invention without limiting its scope.

EXAMPLES

Example 1

Ulipristal Acetate Tablets

A 30 mg ulipristal acetate tablet was prepared, containing the following ingredients.

TABLE 1

30 mg ulipristate acetate tablet:

| Ingredients | Quantity for one tablet (mg) | Quantity for one tablet (wt %) |
|---|---|---|
| Ulipristal acetate | 30.00 | 10 |
| Lactose Monohydrate | 237.00 | 79 |
| Povidone | 15.00 | 5 |
| Croscarmellose sodium | 15.00 | 5 |
| Magnesium stearate | 3.00 | 1 |
| Total | 300.00 | 100 |

Lactose monohydrate 79 wt %, ulipristal acetate 10 wt % and povidone 5 wt % were mixed and purified water was added. This granulation step was immediately followed by a drying step in an oven at 40° C. Then, a calibration step with a Frewitt 630 μm sieve was carried out. Croscarmellose sodium 5 wt % and magnesium stearate 1 wt % were added for the lubrication step. The obtained formulation is compressed to get the tablet.

Further ulipristal acetate tablets are provided hereafter.

TABLE 2

Other ulipristal acetate tablet formulations:

| Ingredients | 10 mg tablet Quantity for one tablet in mg (wt %) | 30 mg tablet Quantity for one tablet in mg (wt %) |
|---|---|---|
| Ulipristal acetate | 10.00 (10) | 30.00 (10) |
| Lactose Monohydrate | 79.00 (79) | 246.00 (82) |
| Povidone | 5.00 (5) | 9.00 (3) |
| Croscarmellose sodium | 5.00 (5) | 12.00 (4) |
| Magnesium stearate | 1.00 (1) | 3.00 (1) |
| Total | 100.00 (100) | 300.00 (100) |

Example 2

Comparison of Bioavailability of a Single 30 mg Oral Dose of Ulipristal Acetate Given in Fed and Fasting States in Healthy Women Materials and Methods Healthy female volunteers (n=18), aged 18 to 35 years old, were administered with single administration of a 30-mg ulipristal acetate micronized tablet of Example 1 (Table 1) either under fasted conditions or after a high-fat breakfast. A second oral administration followed, after at least a 21-day wash-out period.

Analysis of Cmax and AUC was carried out by analysis of variance using PROC MIXED® program on the logarithmically transformed data. The 90% standard confidence interval limits for relative treatment differences was calculated by geometric means based on logarithmic transformation of the intra-individual ratios of Cmax and AUC.

The analysis of $t_{max}$ was based on Wilocoxon-Mann-Whitney test adapted according to the methodology of Koch. Estimate for treatment difference and 90% confidence interval was estimated according to the method of Moses.

Results

Dosing with food significantly reduced the absorption rate of ulipristal acetate (40-45% lower Cmax and by a delay in $t_{max}$ of about 1.5 h for both ulipristal acetate and 3877A) but increased the extent of absorption (20-25% increase in AUC of both ulipristal acetate and of 3877A). Mean concentration-time profiles for ulipristal acetate and 3877A are presented in FIGS. 1-4. The pharmacokinetic parameters and statistical analysis are presented in Table 3 below.

Due to the lack of a reliable log-linear phase, the terminal half-life (and consequently $AUC_{0-\infty}$) could not be estimated in one subject for ulipristal acetate and in three subjects for 3877A when dosed under fasted conditions, and in two subjects of both ulipristal and 3877A when dosed with food.

TABLE 3

Summary of ulipristal acetate and metabolite 3877A pharmacokinetic parameters:

| Parameter | Ulipristal | | 3877A | |
|---|---|---|---|---|
| | Fasted | Fed | Fasted | Fed |
| $C_{max}$ (ng/mL) | 173 ± 68.5 | 99.2 ± 44.3 | 86.5 ± 30.0 | 54.0 ± 21.9 |
| $t_{max}$ (h) | 0.75 (0.50-1.50) | 3.00 (0.50-5.00) | 0.75 (0.50-1.50) | 3.00 (0.50-5.00) |
| $t_{lag}$ (h) | 0.00 (0.00-0.00) | 0.00 (0.00-0.50) | 0.00 (0.00-0.00) | 0.00 (0.00-0.50) |
| $AUC_{0-t}$ (h·µg/mL) | 0.467 ± 0.243 | 0.566 ± 0.285[a] | 0.244 ± 0.0836 | 0.294 ± 0.0934[a] |
| $AUC_{0-\infty}$ (h·µg/mL) | 0.474 ± 0.256[a] | 0.608 ± 0.292[b] | 0.265 ± 0.0834[c] | 0.310 ± 0.0912[b] |
| $t_{1/2}$ (h) | 37.2 ± 7.19[a] | 36.0 ± 7.78[b] | 30.0 ± 7.56[c] | 28.9 ± 6.84[b] |

Values are means ± SD, except median (range) for $t_{max}$ and tlag
NA: not applicable
n = 18, except
[a]n = 17,
[b]n = 16,
[c]n = 15

Cmax was markedly lower under fed conditions, both for ulipristal acetate (99.2 vs 173 ng/mL) and for 3877A (54.0 vs. 86.5 ng/mL). No absorption delay (lag-time) was observed in fasted condition while a short lag-time (max 30 min) was observed in a few subjects when administered under fed conditions. For both ulipristal and 3877A, the peak was markedly delayed following food intake (medians: 3 vs 0.75 h). AUCs were increased by food intake, for ulipristal acetate ($AUC_{0-t}$: 0.566 vs 0.467 h·µg/mL and $AUC_{0-\infty}$: 0.608 vs. 0.474 h·µg/mL) as well as for 3877A ($AUC_{0-t}$: 0.294 vs 0.244 h·µg/mL and $AUC_{0-\infty}$: 0.310 vs. 0.265 h·µg/mL).

The terminal elimination phase started approximately 24 postdose for both treatments. Based on the log-linear mean profiles, the elimination rate seemed similar for both treatments. The terminal elimination half-life averaged around 36 h for ulipristal acetate and around 30 h for 3877A, independently of the food condition. Table 4 below provides a statistical comparison of ulipristal acetate and 3877A pharmacokinetic parameters between treatments.

TABLE 4

Statistical comparison of ulipristal acetate and 3877A pharmacokinetic parameters between treatments:
Fed vs. Fasted condition

| Parameter | Ulipristal | | | 3877A | | |
|---|---|---|---|---|---|---|
| | PE | 90% CI | p-value | PE | 90% CI | p-value |
| $C_{max}$ (%) | 56.25 | 47.85; 66.14 | <0.001 | 62.45 | 50.50; 77.22 | 0.001 |
| $AUC_{0-t}$ (%) | 123.30[a] | 112.62; 134.98 | 0.001 | 121.72[a] | 111.46; 132.91 | 0.001 |
| $AUC_{0-\infty}$ (%) | 126.20[b] | 115.70; 137.64 | <0.001 | 118.73[c] | 108.09; 130.42 | 0.006 |
| $t_{max}$ (h) | 1.63 | 1.00; 2.25 | <0.001 | 1.50 | 0.88; 2.13 | <0.001 |

PE and CI: Point Estimate and 90% CI of the fed/fasted ratio of least squares geometric means (ANOVA), except for $t_{max}$ non-parametric estimate and 90% CI (confidence interval) for the treatment difference.
NA: not applicable
n = 18, except
[a]n = 17,
[b]n = 16,
[c]n = 15

In fed condition, concentration peak fell by an estimated 40-45% and time to peak was delayed by approximately 1.5 h. Administration after a high-fat breakfast resulted in an increase by 20-25% of the extent of absorption in comparison to the administration in fasted condition. These differences observed for both ulipristal acetate and its monodemethylated metabolite 3877A were all statistically significant.

Example 3

Analysis of a Potential Impact of Food Intake on Efficacy of a Single 30 mg Oral Dose of Ulipristal Acetate With respect to clinical efficacy, data on last food intake prior to study drug was collected in a subset of subjects (n=1185) included in the phase III program of development of the 30 mg ulipristal acetate tablet for emergency contraception. Pregnancy rates (PR) were compared between women who reported having eaten within two hours prior to treatment intake versus those who reported having eaten only earlier. Table 5 shows that there was no significant effect of food consumption prior to ulipristal acetate intake on pregnancy rate in the phase III trials.

TABLE 5

Pregnancy rates observed and expected after ulipristal acetate treatment by food consumption:

| Food intake | Number of subjects (ulipristal acetate) N = 2180 | Observed PR, % (95% CI) | Expected PR, % |
|---|---|---|---|
| Less than 2 h before ulipristal acetate intake | 279 | 1.79% (0.65-4.25) | 5.27% |
| 2 h or more before ulipristal acetate intake | 905 | 1.44% (0.82-2.47) | 5.56% |
| p* | | p = 0.779 | |

*Comparison among the 2 groups, Fischer's exact test

The invention claimed is:

1. A method for providing emergency contraception in a female subject, comprising the step of administering to the subject after unprotected intercourse a therapeutically effective amount of ulipristal acetate ranging from about 20 mg to about 30 mg in an oral dosage form with food.

2. The method of claim 1 wherein the ulipristal acetate is administered before or after food ingestion.

3. The method of claim 1 wherein the food has a high fat content.

4. The method of claim 1 wherein the oral dosage form is a tablet.

5. The method of claim 1 wherein the dosage form comprises 30 mg ulipristal acetate.

6. The method of claim 1, wherein ulipristal acetate is administered to the subject within 72 hours after unprotected intercourse.

7. The method of claim 1, wherein ulipristal acetate is administered simultaneously with food ingestion.

8. The method of claim 1, wherein the oral dosage form is a tablet comprising from 3% to 18% by weight of ulipristal acetate, from 60% to 95% by weight of a diluent, from 1% to 10% by weight of a binding agent, from 1% to 5.5% by weight of croscarmellose sodium and 1% to 4% by weight of magnesium stearate.

9. The method of claim 1, wherein the administration of ulipristal acetate with food results in an about 40-45% decrease in mean $C_{max}$, an about 20-25% increase in mean $AUC_{0-\infty}$ and a delayed median $t_{max}$ by at least about 1.5 hours as compared with administration of ulipristal acetate without food.

* * * * *